United States Patent [19]

Fussi et al.

[11] 4,143,132

[45] Mar. 6, 1979

[54] POLYANION FRACTION CONTAINING HEXOSAMINES

[76] Inventors: Fernando Fussi, Via Ugo Foscola 31, Lesmo (Milan); Gianfranco Fedeli, Via Zanta 19, Milan, both of Italy

[21] Appl. No.: 701,736

[22] Filed: Jun. 30, 1976

[30] Foreign Application Priority Data

Jul. 3, 1975 [IT] Italy .............................. 25065 A/75

[51] Int. Cl.² .......................................... A61K 35/38
[52] U.S. Cl. ................................................. 424/104
[58] Field of Search ........................................ 424/104

[56] References Cited

U.S. PATENT DOCUMENTS

| | | | |
|---|---|---|---|
| 2,276,882 | 3/1942 | Schneiderwirth | 424/104 |
| 3,000,787 | 9/1961 | Bianchini | 424/104 |
| 3,174,033 | 3/1965 | Fischer et al. | 424/104 |

*Primary Examiner*—Sam Rosen
*Attorney, Agent, or Firm*—Cushman, Darby & Cushman

[57] ABSTRACT

From the residual liquors of the extraction of active principles, particularly heparin, from animal organs, a fraction of natural polyanions is obtained having, besides clearing and anticoagulant activity, also antiphlogistic and anti-inflammatory activity as well as stimulating activity on the reticuloendothelial system, whereby it is useful in the treatment of atherosclerosis and related diseases. The process for obtaining these natural polyanions is also disclosed.

4 Claims, No Drawings

POLYANION FRACTION CONTAINING HEXOSAMINES

The main object of the present invention is an extraction fraction, which hereinafter shall be indicated by natural polyanions NHP (NHP = natural heparin-like polyanions), which are distinguished from heparin and present in the solution of extraction of active principles from animal organs.

More particularly, an object of the present invention are the natural polyanions found in the residual liquors of the extraction of heparin.

Another object of the present invention is a process for the isolation and the purification of these natural polyanions.

A further object of the present invention resides in the therapeutical uses of the said natural polyanions and thus in the pharmaceutical compositions containing them as the active ingredient.

The more recent theories on the pathogenesis of the vascular ischemias and of the atherosclerosis assign an important role to the immunological and inflammatory factors.

According to this point of view, the arteritis, as a cause of lipidic infiltration, finds a logical explanation in the fact that the inflammation, by causing the endothelial permeability to be increased, induces a greater amount of lipidic substance to penetrate. In turn, the arteritis is liable to have an immunological origin, immunocomplexes being in fact used for inducing experimental arteritis and such a treatment, when combined with a lipidic diet, causing the atherosclerotic symptoms to rapidly appear. For this reason, much literature exists on experimental work carried out by using substances having anti-inflammatory activity and acting on the immunity system in order to inhibit the atherosclerosis from being induced in the animal; amongst these substances the following can be cited: histamine, serotonin, angiotensin, adrenaline, pyridinole carbamate, chlorpheniramine, phenylbutazone, amidopyrine, aspirin, corticosteroids, cyclophosphamide.

To date in the field of the cardio-vascular diseases of ischemic origin the only natural polyanionic substances of macromolecular type which found a therapeutical use were heparin (always administered by oral route) and other sulfurated mucopolysaccharides, called "heparinoids" (some being also active per os); the common effects to which the activities of these substances in the specific field of therapeutical use are to be attributed, are as follows: (a) the activation of the lipoprotein-lipase enzyme, which accelerates the metabolism of the serum lipids, giving place to a so-called "clearing" effect; (b) an anticoagulant activity, highly remarkable in the case of heparin, but lower in the case of the heparinoids, having as its effect an action antagonizing the building up of intramural thrombi.

It has now been surprisingly found that a polyanionic fraction, as obtained by extraction from animal organs and indicated as natural polyanions (NHP), is endowed, besides the clearing activity shown by heparin and the heparin-like substances, with a mild anticoagulant activity, which is specific for the heparinoids, with antiphlogistic and anti-inflammatory activity and with stimulating activity with respect to the reticuloendothelial system (RES). Another feature of the present invention resides in that said natural polyanions are obtained by isolation and purification from the residual liquors remaining in the extraction of heparin as well as from every other extracting solution, resulting in the extraction of active principles from animal organs, provided that in these solutions proteic or peptidic material having high molecular weight or substances forming stable bonds with said natural polyanions are substantially absent.

The identification of the fraction of natural polyanions of the present invention is based on the precipitability from neutral aqueous solutions on addition of quaternary ammonium salts. The precipitate, recovered and suspended in water, is again solubilized by adding NaCl when the concentration of the salt is 1 M.

Other data of the NHP fraction are the following:
hexosamines after hydrolysis (reaction with p-phenylendiamine): $7 \pm 2$
hexuronic acids after hydrolysis (reaction with carbazole): $5 \pm 1.5$
organic $SO_4^{--}$ after hydrolysis (reaction with naphtharsone): 4.5 —9
average molar ratio hexosamines/uronic acids/$SO_4^{--}$: 1.2/1/2.4
ribose after hydrolysis (reaction with orcine): present
desoxyribose after hydrolysis (reaction with diphenylamine): present
organic phosphorus after hydrolysis (reaction with molybodenum blue): $6 \pm 2$
average ratio pentoses/organic phosphorus: 1/1
peptides and proteins (reaction with biuret): absent
electrophoresis on cellulose acetate with pyridine (1), acetic acid (10), water (229) buffer, pH 4.5
a. development with toluidine blue: three bands
b. development with "Alcian blue": one-two bands
Spectrophotometric data:
$\lambda \text{ max} = 260 \pm 1$ nm $\lambda \text{ min} = 230 \pm 1$ nm Solubility:
a. in water: soluble with opalescence
b. in mineral acids: a precipitate is formed
c. in fixed alkali: soluble with opalescence.

The natural polyanion fraction can be obtained from animal organs, particularly intestinal mucosa, after the raw heparin has been precipitated according to any of the classical methods.

The residual liquors, after the heparin precipitation show roughly the following composition:
solid residue: 20–22 mg/ml
peptides: 60–70% (on dry basis)
other organic substances: 20–25% (on dry basis)
inorganic salts: 10–15% (on dry basis)
pH: 8.

The process according to the present invention is more particularly characterized by the following steps:
a. precipitation of the polyanions present in the said liquors in the presence of an excess of about 10% by weight referred to the polyanions, namely about 0.25% by weight referred to the liquors, of a quaternary ammonium base (such as for example cetylpyridinium chloride, cetyltrimethylammonium bromide, etc.);

b. solubilization of the precipitate in a solution of one or more inorganic salts of a mono- or bi-valent cation and then final precipitation of the sought fraction by addition of a water miscible solvent (for example ethanol, methanol, acetone).

There can be added an excess of 0.2 to 0.5% by weight of a quaternary ammonium base, based on the liquors.

The following examples illustrate more particularly the extraction process for the natural polyanion fraction of the present invention.

EXAMPLE 1

36 liters of deheparinized liquors were treated with 3 liters of a 5% solution of cetyltrimethylammonium chloride.

After standing for 24 hours at room temperature, the precipitate was recovered by centrifugation and suspended in a 1.5 M KCl solution. After filtration, 2.5 volumes of acetone were added to the clear liquid. After 24 hours standing the precipitate was recovered on a Buchner filter, dehydrated with acetone and ether and dried under vacuum. 2 grams of natural polyanions were obtained, with the following composition: Hexosamine: 5.6%; hexuronic acids: 6.3%; organic phosphorous: 5.85%; $SO_4^{--}$: 8.1%; electrophoresis: three bands with toluidine blue and two bands with Alcian Blue; $E_{1cm}^{1\%}$ at 260 nm = 175.

EXAMPLE 2

100 liters of deheparinized liquors, adjusted to pH 8, were heated to 45° C. and treated with 5 liters of 8% cetylpyridinium chloride heated at 45° C. The mixture was maintained under these conditions for 2 hours. Then the precipitate was recovered on a hot Buchner filter, 100 grams of standard Supercel being added; the filter cake was washed with 2 liters of hot water and dried. The filter was dispersed in 2 liters of a 1M $MgSO_4$ solution, the mixture being then heated to 40° C. for one hour and filtered. The clear filtrate was treated under stirring with two volumes of methanol. After standing for some hours the supernatant liquid was separated and the precipitate was dehydrated with a mixture of methanol, acetone and ether; then it was dried under vacuum at 40° C.

Yield: 6 grams of natural polyanions having the following composition:

Hexosamine: 4.1%
Hexuronic acids: 7%
Organic phosphorus: 6.3%
$SO_4^{--}$: 4.2%
Electrophoresis: three bands with toluidine blue, and one band with Alcian Blue.
$E_{1\,cm}^{1\%}$ at 260 nm: 160.

The fraction of natural polyanions, as above identified, was tested in order to determine the bio-pharmocological properties and activities, with the following results:

Toxicological tests: NHP is a natural product, having no toxic effects when administered to mice, rats and rabbits, both per os and by the parenteral route, as well as even topically, up to dosages of 200 mg/kg of body weight.

Activation of the serum lipoprotein-lipase (emulsion of triglycerides and rat serum treated with the substance): 3 ± 1 lipasemic U/mg Antiinflammatory and antiphlogistic activity: at a dosage of 100 mg/kg of body weight, on subcutaneous administration, the NHP fraction was active in inhibiting the plantar edema, as induced both by trypsin and by egg white, like that of an equal dosage of heparin USP.

Anticoagulant activity = 15 ± 5 I.U.

Protection against intoxication by carbon tetrachloride (measurement of the biliary secretion of the bromosulphophtalein, method of Savel) = 150 ± 50 Savel u/g.

As the possible therapeutical uses of the (NHP) natural polyanion fraction, at dosages of 60–120 mg/day, either per os or by parenteral route, the following are indicated: prevention of the atherosclerosis and of the more frequent complications, such as the myocardial infarction, the cerebral ictus, and the occlusion of the peripheral arteriae; the regression, in amplit de and gravity, of the lesions of the arterial walls in the course of the atheromatous and atherosclerotic process; secundary prevention of the infarction repetition in the patients already affected by infarction.

What we claim is:

1. A process for obtaining a fraction of natural polyanions from residual liquors of heparin extraction comprising adding an excess of 0.2 to 0.5% by weight, based on the liquors, of a quaternary ammonium base to form a precipitate, solubilizing the precipitate with a solution of a salt of a mono- or bi-valent cation, and then precipitating the fraction by adding a water miscible solvent.

2. A process according to claim 1 wherein the water miscible solvent is methanol, ethanol or acetone.

3. A process according to claim 1 wherein said residual liquors are obtained from heparin extraction from intestinal muscosa.

4. The product prepared by the process of claim 1.

* * * * *